(12) United States Patent
Newman

(10) Patent No.: US 11,813,351 B2
(45) Date of Patent: Nov. 14, 2023

(54) BEAUTY PRODUCT COMPOSITION FOR EYEBROWS

(71) Applicant: Stella Grace Newman, Mays Landing, NJ (US)

(72) Inventor: Stella Grace Newman, Mays Landing, NJ (US)

( * ) Notice: Subject to any disclaimer, the term of this patent is extended or adjusted under 35 U.S.C. 154(b) by 166 days.

(21) Appl. No.: 17/102,262

(22) Filed: Nov. 23, 2020

(65) Prior Publication Data

US 2022/0160616 A1    May 26, 2022

(51) Int. Cl.
| | |
|---|---|
| *A61K 8/92* | (2006.01) |
| *A61K 8/98* | (2006.01) |
| *A45D 40/06* | (2006.01) |
| *A61Q 7/00* | (2006.01) |

(52) U.S. Cl.
CPC .............. *A61K 8/922* (2013.01); *A45D 40/06* (2013.01); *A61K 8/987* (2013.01); *A61Q 7/00* (2013.01); *A61K 2800/87* (2013.01)

(58) Field of Classification Search
None
See application file for complete search history.

(56) References Cited

U.S. PATENT DOCUMENTS

| | | | | |
|---|---|---|---|---|
| 1,493,777 | A | * | 5/1924 | Goertz ................... A45D 40/02 401/82 |
| 2,201,467 | A | | 5/1940 | Israel |
| 9,066,952 | B1 | * | 6/2015 | Brown ................. A61K 8/9794 |
| 2018/0250213 | A1 | * | 9/2018 | Okunishi ................. A61Q 7/00 |

FOREIGN PATENT DOCUMENTS

| | | |
|---|---|---|
| CN | 105106028 A | 12/2015 |
| CN | 106389298 A | 2/2017 |
| FR | 2850548 A1 | 8/2004 |
| JP | 5597233 B2 | 10/2014 |
| KR | 101071984 B1 | 10/2011 |
| KR | 102065949 B1 | 1/2020 |
| WO | 2018080282 A1 | 5/2018 |

* cited by examiner

*Primary Examiner* — Nannette Holloman
(74) *Attorney, Agent, or Firm* — Howard University School of Law; Darrell G. Mottley

(57) ABSTRACT

A composition for stimulating eyebrow growth is provided. The composition includes about black Jamaican oil with lavender, about one tablespoon and about a half teaspoon raw cacao powder, about one tablespoon raw shea butter, about one tablespoon yellow beeswax, and about one tablespoon cedarwood oil. The composition may be formed in a solid form and is used as a stick. The stick may be used as a lipstick or eyebrow applicator.

9 Claims, 2 Drawing Sheets

| COMPOSITION 100 | QUANTITY |
|---|---|
| Black Jamaican Oil With Lavender | 1 ts |
| Raw Cacao Powder | 1.5 ts |
| Raw Shea Butter | 1 ts |
| Yellow Beeswax | 1 ts |
| Cedarwood Oil | 1 ts |

FIG. 1

BEAUTY PRODUCT COMPOSITION FOR EYEBROWS

FIELD

The present disclosure generally relates to a beauty product composition, and particularly relates to a beauty product composition for hair growth and tinting eyebrow.

BACKGROUND

Personal care formulations are available in a wide range of formulation forms and are used in a wide variety of specialized applications. Because these various types of formulations differ enormously, as do the conditions under which they are used, the individual formulations tend to be formulated specifically for the end-use application for which they are intended. Most at home brow hair dye Is made with harsh chemicals that can break and damages the brow hair.

Human skin color is quite variable around the world. It ranges from a very dark brown among some Africans, Australians and Asian-Indians to a near pinkish yellow among some northwest Europeans. There are no people who truly have black, white, red or yellow skin. These are commonly used terminologies that do not reflect biological reality. Skin coloration in humans arises from a complex series of cellular processes that are carried out within that population of cells known as the melanocytes located in the lower part of the epidermis. These processes result in the synthesis and transfer of a pigment, melanin, which, besides being responsible for skin color and tone, is the key physiological defense against sun-induced damage, such as sunburn, photoaging and photocarcinogenesis.

The eyebrows or eyelashes frame the upper margin of the eye orbit and are a feature of the facial landscape. These eyebrows or eyelashes differ from other parts of hair, such as the hair of the scalp, in terms of the period of growth and rest periods. Eyebrow hypotrichosis, also known as madarosis, is characterized by a lack of growth or loss of eyebrow hair. Eyebrow loss can have cosmetic, functional, and social consequences. Eyebrow hypotrichosis can be idiopathic or related to an underlying condition. Loss of eyebrow hair is common among men and women. In many instances, thinning of the eyebrows can be attributed to regular removal of eyebrow hair, which is particularly common for women who pluck their eyebrows for aesthetic purposes. Eyebrow thinning may also result from include excessive plucking and rubbing resulting from a nervous habit, or medical conditions wherein patients experience eyebrow hair loss as a side effect of treatment. The current products have not produced desired effects in desired time.

SUMMARY

This summary is provided to introduce a selection of concepts in a simplified form that are further described below in the Detailed Description. The Summary is not intended to identify key features or essential features of the claimed subject matter, nor is it intended to be used to limit the scope of the claimed subject matter.

In accordance with teachings of the present disclosure, a composition of natural ingredients to grow and tint eyebrow hair is provided. In accordance with teachings of the present disclosure, the composition can tint of the eyebrow hair of lighter shades without substantially staining the skin beneath.

An aspect of the present disclosure is to provide a composition for stimulating eyebrow growth, the composition comprising: black Jamaican oil with lavender; raw cacao powder; raw shea butter; yellow beeswax; and cedarwood oil.

An aspect of the present disclosure is to provide a composition having about one part black Jamaican oil with lavender, about one and one-half part raw cacao powder, about one part raw shea butter, about one part yellow beeswax, and about one part cedarwood oil based on volume on 5.5.

An aspect of the present disclosure is to provide a composition having about one tablespoon black Jamaican oil with lavender, about one tablespoon and about a half teaspoon raw cacao powder, about one tablespoon raw shea butter, about one tablespoon yellow beeswax, and about one tablespoon cedarwood oil based on a volume of about 5.5 ounces. The composition described in the present disclosure may be an eye balm provided in a solid formulation.

Another aspect of the present disclosure is to provide a stick in a form of lipstick or eyebrow applicator containing the composition from natural ingredients to grow and tint eyebrow hair of a human body.

Another aspect of the present disclosure provides a method of stimulating eyebrow growth, including periodically administering a composition consisting of: black Jamaican oil with lavender, raw cacao powder, raw shea butter, yellow beeswax, and cedarwood oil; to an eyebrow of a human body.

All publications and patent applications mentioned in this specification are herein incorporated by reference to the same extent as if each individual publication or patent application was specifically and individually indicated to be incorporated by reference.

BRIEF DESCRIPTION OF DRAWINGS

FIG. 1 shows a table of composition of natural ingredients for growing and tinting eyebrow hair according to certain aspects of the present disclosure;

DETAILED DESCRIPTION

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings.

A "dermatologically acceptable carrier" refers to a material that acts as a vehicle or carrier for the stated actives, and is recognized in the industry as acceptable or suitable for use, preferably long term use, in skin contact and, most preferably, without undue toxicity, incompatibility, irritability, allergic response and the like. Typically and to the extent appropriate or applicable, dermatologically acceptable carriers include those carriers that have been approved or are otherwise approvable by a regulatory agency of a government or governmental body or that are listed in the U.S.

Pharmacopoeia or other generally recognized pharmacopoeia for use on humans. As used herein the term carrier also refers to base compositions used in formulating cosmetic, skin care, skin therapy and topical pharmaceutical products as well as such products themselves.

The terms "improves" and "improved" is used to convey, when referencing the eye brow hair and performance of the claimed compositions and methods, that there is a noticeable hair grow in those areas of the skin to which the composition is applied and, when referencing cosmetic and other skin care products and compositions, that the application of the product or composition provides a noticeable eye brow hair growth in the area(s) to which the product or composition has been applied.

Terms of degree such as "generally", "substantially", "about" and "approximately" as used herein mean a reasonable amount of deviation of the modified term such that the end result is not significantly changed. For example, these terms can be construed as including a deviation of at least +−0.5% of the modified term if this deviation would not negate the meaning of the word it modifies.

Figure 3:
FIG. 3 shows an example of the before and after uses of the composition of natural ingredients for growing and tinting eyebrow hair on a human body.

The following example will illustrate a method of preparing this natural compound in accordance with the present disclosure although; as will be evident to those skilled in the art, various equivalent substances may be used, in place of those mentioned and various equivalent procedures may be used instead of the particular steps described. As an example of the use of these materials a composition 100 particularly suitable for use as a growing eyebrow hair as shown in FIG. 3 may be made as follows, FIG. 1 shows a table of composition 100 of natural ingredients for growing and tinting eyebrow hair. Composition 100 can stimulate eyebrow growth, the composition may consist of: black Jamaican castor oil with lavender; raw cacao powder; raw shea butter; yellow beeswax; and cedarwood oil. In accordance with teachings of the present disclosure, a composition 100 of natural ingredients to grow and tint eyebrow hair is provided. In accordance with teachings of the present disclosure, the composition 100 can tint of the eyebrow hair of lighter shades without substantially staining the skin beneath. In an aspect of the present disclosure, composition 100 includes essentially about 15-20 percent by volume black Jamaican castor oil with lavender, essentially about 25-30 percent by volume raw cacao powder, essentially about 15-20 percent by volume raw shea butter, essentially about 15-20 percent by volume yellow beeswax, and essentially about 15-20 percent by volume cedarwood oil.

In an aspect of the present disclosure, composition 100 includes preferably about 20 percent by volume black Jamaican castor oil with lavender, preferably about 30 percent by volume raw cacao powder, essentially about 20 percent by volume raw shea butter, preferably about 20 percent by volume yellow beeswax, and preferably about 20 percent by volume cedarwood oil. The natural ingredients are mixed.

As an example of the use of these materials a composition 100 particularly suitable for use as a growing eyebrow hair may be made as follows. The composition 100 includes about one tablespoon black Jamaican castor oil with lavender, about one tablespoon and about a half teaspoon raw cacao powder, about one tablespoon raw shea butter, about one tablespoon yellow beeswax, and about one tablespoon cedarwood oil which can make about a sufficient quantity sticks 200 (such as 5-10 sticks depending on the mold size) containing the composition 100 (see FIG. 2). In this method of preparing this natural composition 100 in accordance with the present disclosure has each stick 200 may have about a net weigh of 3.4 oz.

In one method of preparation, each ingredient is measure out with metal measuring spoons (other acceptable method) and the ingredients are placed into a metal container that is heated with a double boiler method for a few minutes until the beeswax and Shea butter is melted. The product is stirred and poured directly into the silicone bullet shaped molds to form a stick 200. The molds are placed directly into a freezer for rapid cooling. Of course, the molds could be placed in an appropriate refrigerator system. The minimum time the beauty product needs to set up to become solid is about 15 minutes. The beauty products can be retained in the freezer until the product stick 200 are shipped. Then, product bullet is removed from the silicone mold to form the product in applicator form. The composition 100 has the structural integrity of a solid and therefore can retain a shape and can be molded into a cylindrical shape with the silicone bullet shape mold.

Referring to FIG. 1, Jamaican black castor oil has been used by Caribbean women to moisturize, thicken, strengthen and rapidly increase hair growth. It is said to increase blood flow to the scalp, supplying valuable nutrients to hair follicles, and prevent hair breakages, dandruff, eczema and dry, itchy scalp. Jamaican black castor oil is also known as black castor oil or by its INCI name, *Ricinus communis* seed oil. It is considered to be an all-purpose personal care healing oil, commonly used for hair and scalp problems (see U.S. Pat. No. 9,066,952 B1 incorporated by reference herein) in the Caribbean.

The oil seals moisture in the hair with a protective coat. Jamaican black castor oil is rich in the fatty acid triglyceride ricinoleic acid, which is thought to be responsible for its healing abilities. Ricinoleic acid is an effective topical treatment for pruritus (itching) of the scalp. Ricinoleic acid also possesses analgesic and anti-inflammatory activity and is thought to increase blood flow to where it is applied. Ricinoleic acid is also said to help balance scalp pH, which may also help replenish the scalp and natural oils and undo some of the damage of harsh chemical hair products (and even damage from no-poo shampoo, due to over alkalinity). The antioxidants in Jamaican black castor oil are also said to support the keratin in hair and to aid in making hair stronger, smoother and less frizzy.

Referring to FIG. 1, the raw cacao powder adds natural brown/taupe color with major antioxidants to boot. The cacao powder tends to have a red tint, roasted tends to have a deeper, ashier hue. The raw shea butter keeps the hair follicles moisturized and makes sure that they are getting enough nutrition to grow with full zeal. The cacao powder in the composition 100 safely and temporarily dyes brow hair up to 2 shades in 2-3 overnight treatments, Shea coats hair follicles and provides them with insane nutrients and hydration. This has the ability to make hair appear fuller and thicker even the first use and provides instant volume.

The yellow beeswax has the characteristics of good adhesion, permeability, emulsibility, smoothness and the like and has the effects of beautifying, moistening, protecting and removing wrinkles and the like, and is applied to the production of cosmetics such as cream, lipstick, rouge, hair oil, pomade, eyebrow pencil, eye shadow, emulsion and the like.

Beeswax constitutes honeycomb cells and is mainly comprised of even- and odd-chain saturated and unsaturated hydrocarbons, monoesters of palmitic, oleic and hydroxypalmitic acids. There are chemical analyses apt to distinguish virgin beeswax from wax adulterated by paraffin. Beeswax is produced by worker bees who form a honeycomb to store honey for the colony. Moisturizing vitamin A is found in beeswax along with small amounts of antibacterial agents. Yellow beeswax provides moisture, smooth & straighten, seal strands, and promote hair growth. (Beeswax can be use in lip stick—see U.S. Pat. No. 10,376,547 B1 incorporated by reference herein). Cedarwood essential oil promotes hair growth and reduce hair loss by balancing the oil-producing glands in the scalp. Cedarwood oil has antifungal and antibacterial properties, that contributes to treating dandruff or hair loss.

Figure 2:
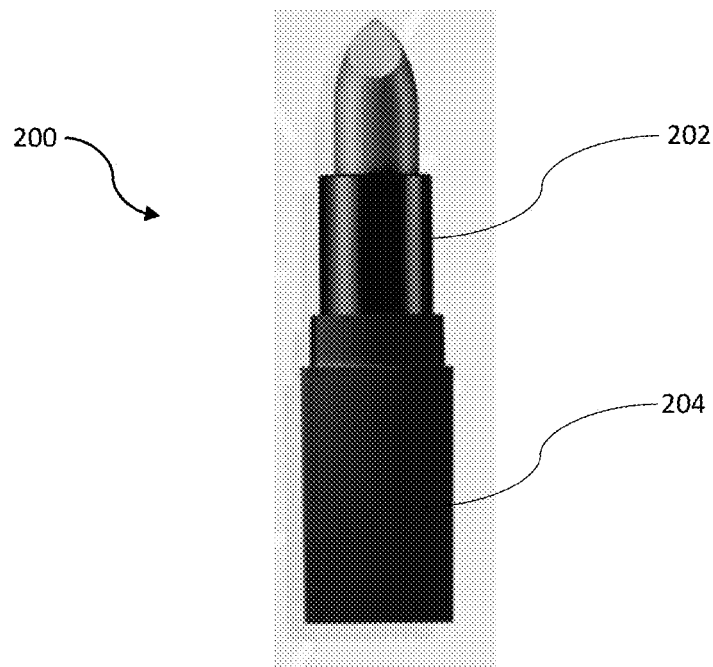
FIG. 2 illustrates a perspective view of a retractable stick apparatus containing a composition of natural ingredients for growing and tinting eyebrow hair according to certain aspects of the present disclosure may implemented.

FIG. 2 illustrates a view of a stick 200 containing a composition 100 of natural ingredients for growing and tinting eyebrow hair. The composition 100 may be provided in any suitable form. The composition 100 in the present disclosure may be an eye balm provided in a solid formulation or a semisolid formulation useful for topical use on humans. Most preferably, the composition is provided in the form of a solid stick shown in FIG. 2 of a substantially uniform and homogenous admixture. The composition 100 has the structural integrity of a solid and therefore can retain a shape and can be molded into a cylindrical shape. The stick 200 may be applied through the use of an eyebrow applicator that has a receptacle 202 for a pre-shaped cylinder tint stick of the eyebrow product. Nevertheless, the implementation may include other embodiments and/or variations of that shown in FIG. 2. The composition 100 may have a shape different from the cylinder shape shown in FIG. 2. For example, the composition 100 may be curved in a solid hemisphere or have a different geometric or non-geometric shape.

The receptacle 202 sits on a rotatable base 204 which moves the stick vertically up and down with a twist and the like. The receptacle may be a recessed member designed to hold a portion of one end of the eye brown stick having the composition 100. The remainder of the stick extends from the receptacle. The receptacle reposes in a mechanism for extending and retracting the tint stick from the applicator as product is to be used or to store the stick when it is not being applied. When a tint stick 200 is initially purchased, the stick 200 is pre-shaped to a point or the stick is angled to permit the user to apply the tint stick in the desired manner. In one construction, there is provided a cylindrical housing 202 with an interior comprising the composition 200, a removable cap (not shown), and a dispensing mechanism in the form of a twistable knob 204 to remove the composition vertically out of the housing 202.

Example 1

As an example of the use of these materials, a composition 100 is particularly suitable for use as a growing eyebrow hair as shown in FIG. 3. Nevertheless, as also discussed in detail below, the disclosure entails a method of applying composition 100 to the eye brows of a person, by providing a stick 200 having the features as discussed herein, placing a top end portion of the stick 200 on top of eye brows, with the eye brows of the person being in contact with the stick 200 and moving the stick 200 sideways relative to the brow of the person so that portions of composition 100 are applied to portions of the eye brow of the person.

In one method of treatment to the eyebrows, the before eyebrow image and after eyebrow image is subsequent to three nights a week for five weeks (e.g., 15 periodic applications of the composition) to the eyebrows of a human subject. The composition 100 in the form of a solid balm was topically administered 2-3 times over the brows. Then, the brows were slightly brushed up to brush way excess balm on the skin. Grey hair can be tinted as well. The human subject was informed that improvement in her eyebrow hypotrichosis should be gradual. Periodic follow-up weekly was generally performed. At each follow-up, the subject reported using the composition once a day for three nights application per week on the eye brows. A darker color change in the eyebrow hair was observed. After about five weeks, surprising results of increased hair growth and thickening of the eyebrow area was observed. Because the product is of natural ingredients had no treatment-associated side effects.

Example 2

The duration and frequency of application was a once a day for seven days a week for five weeks or about 35 periodic applications of the composition. The composition 100 in the form of a solid balm was topically administered 2-3 times over the brows. After about five weeks, increased hair growth and thickening of the eyebrow area was observed. Because the product is of natural ingredients had no treatment-associated side effects.

The present disclosure offers various advantages such as stimulating and promoting healthy eyebrows with natural tint. The composition may be formed as a stick (or cream in other implementations) to be applied to eyebrows. The composition use doubles tint for eyebrows of lighter shades without staining the skin beneath and also a growth serum to promote slow growth of the eyebrow hair overtime.

The term "semisolid" refers to a composition which, at room temperature, i.e. at a temperature of about 59° F. to 77° F., has the consistency of a cream, ointment or paste. Thus, a semisolid may not be free flowing in the same way as a liquid.

Although the topical composition first designed for stimulating eye brow hair, and thus is particularly suited for use as an eye balm, the special properties of the topical composition the it suitable for use in a number of other cosmetic and medical applications. Although the compositions and methods of the present specification as well as various commercial and consumer products containing/comprising the same have been described with respect to specific embodiments and examples, it should be appreciated that the present teachings are not limited thereto and other embodiments utilizing the concepts expressed herein are intended and contemplated without departing from the scope of the present teaching as intended in the true spirit and scope of the invention. It is therefore intended any and all modifications, variations, or equivalents that fall within the spirit and scope of the underlying principles are within the scope of this invention and are covered by the appended claims.

What is claimed is:

1. A composition for stimulating eyebrow growth, the composition comprising:
   20 percent by volume of black Jamaican oil with lavender;
   30 percent by volume of raw cacao powder;
   20 percent by volume of raw shea butter;
   15 percent by volume of yellow beeswax; and
   15 percent by volume of cedarwood oil; wherein percentages are based on the total weight of the composition.

2. An applicator apparatus for stimulating eyebrow growth, the applicator apparatus comprising:
   a receptacle for storing a composition in solid form, the composition including: 20 percent by volume of black Jamaican oil with lavender; 30 percent by volume of raw cacao powder; 20 percent by volume of raw shea butter; 15 percent by volume of yellow beeswax; and 15 percent by volume of cedarwood oil; wherein percentages are based on the total weight of the composition; and a rotatable base configured to vertically extend the composition out of the receptacle for application.

3. The applicator according to claim 2, wherein the receptacle further comprises a cylindrical housing.

4. The applicator according to claim 2, wherein the composition comprises a cylindrical shape.

5. A method of stimulating eyebrow growth, the method comprising: topically administering a composition including 20 percent by volume of black Jamaican oil with lavender; 30 percent by volume of raw cacao powder; 20 percent by volume of raw shea butter; 15 percent by volume of yellow beeswax; and 15 percent by volume of cedarwood oil; wherein percentages are based on the total weight of the composition; to an eyebrow of a human body.

6. The composition according to claim 5, wherein the composition is in the form of a solid.

7. The composition according to claim 5, wherein the composition is in the form of a semisolid.

8. The composition according to claim 1, wherein the composition is in the form of a solid.

9. The composition according to claim 1, wherein the composition is in the form of a semisolid.

\* \* \* \* \*